(12) United States Patent
Wandler

(10) Patent No.: US 10,357,172 B2
(45) Date of Patent: Jul. 23, 2019

(54) ELECTRODE LEAD WIRE CONNECTOR

(71) Applicant: Technical Services for Electronics, Inc., Arlington, MN (US)

(72) Inventor: David Wandler, Necedah, WI (US)

(73) Assignee: TECHNICAL SERVICES FOR ELECTRONICS, INC., Arlington, MN (US)

( * ) Notice: Subject to any disclaimer, the term of this patent is extended or adjusted under 35 U.S.C. 154(b) by 1377 days.

(21) Appl. No.: 14/279,401

(22) Filed: May 16, 2014

(65) Prior Publication Data

US 2015/0327788 A1    Nov. 19, 2015

(51) Int. Cl.
| | |
|---|---|
| *A61B 5/0416* | (2006.01) |
| *A61B 5/0408* | (2006.01) |
| *A61N 1/04* | (2006.01) |
| *H01R 13/627* | (2006.01) |
| *H01R 13/11* | (2006.01) |

(52) U.S. Cl.
CPC ........ *A61B 5/0416* (2013.01); *A61B 5/04087* (2013.01); *A61N 1/048* (2013.01); *H01R 13/6277* (2013.01); *A61N 1/046* (2013.01); *H01R 13/111* (2013.01); *H01R 2201/12* (2013.01)

(58) Field of Classification Search
CPC .............................. A61B 5/0416; A61N 1/048
See application file for complete search history.

(56) References Cited

U.S. PATENT DOCUMENTS

| | | | |
|---|---|---|---|
| 5,454,739 A | 10/1995 | Strand | |
| 5,624,281 A | 4/1997 | Christensson | |
| 7,950,971 B2 | 5/2011 | Hobet et al. | |
| 8,408,948 B2 * | 4/2013 | Selvitelli | A61B 5/0416 439/729 |

* cited by examiner

*Primary Examiner* — Alyssa M Alter
(74) *Attorney, Agent, or Firm* — RatnerPrestia

(57) ABSTRACT

Electrode lead wire connectors configured to be connected to an electrode for defibrillation and/or heart monitoring are disclosed. The electrode lead wire connector includes a one-piece electrically conductive connector contact having one end that is configured to be connected to a lead wire and an opposite end having an electrode receiving section that is configured to releasably receive a post of an electrode. The electrode receiving section includes a detent for retaining the post of the electrode within the electrode receiving section. Resilient engagement between the detent and the post provides a user of the electrode lead wire connector with tactile feedback indicating that the post of the electrode is fully engaged with the electrode receiving section of the one-piece electrically conductive connector contact.

10 Claims, 8 Drawing Sheets

ELECTRODE LEAD WIRE CONNECTOR

FIELD OF THE INVENTION

The present invention generally relates to the field of electrode lead wire connectors for defibrillation and/or heart monitoring.

BACKGROUND OF THE INVENTION

Electrocardiograph (ECG) monitors are medical devices used to identify and record electrical activity associated with the heart and pulmonary system. Medical practitioners have traditionally utilized ECG monitors to diagnose various disorders relating to heart rate abnormalities or heart defects. Since the human body is conductive, electrical activity originating from the heart is transferred throughout the body. The ECG monitors are configured to detect the electrical activity at the surface of a patient's skin.

To detect the electrical activity, ECG monitors utilize ECG electrodes to overcome the electrical impedance of the skin. ECG electrodes often include an electrically conductive component that is placed against the skin. The ECG electrode is traditionally affixed to the patient's body by an adhesive (such as tape). The ECG electrode is connected to an ECG monitor by a wire assembly. The wire assembly includes an electrode connector at one end for releasably connecting to the ECG electrode, and a plug at the other end for connecting to the ECG monitor.

An automated external defibrillator (AED) is a device that monitors the heart rhythm like an ECG monitor, and, if needed, transmits an electric shock to the heart to try to restore a normal rhythm. AEDs may be used to treat sudden cardiac arrest. AED's typically include low-voltage ECG electrodes (like ECG monitors) for monitoring purposes, as well as high-voltage defibrillating electrodes (referred to as AED electrodes) for transmitting the electrical shock to the heart.

One or more ECG electrodes for monitoring heart rate are connected to an AED by a low-voltage wire assembly. The low-voltage wire assembly includes an electrode connector at one end for releasably connecting to the ECG electrode on a patient's body, and a plug at the other end for connecting to the AED. One or more AED electrodes for shocking the heart are also connected to an AED by a high-voltage wire assembly. The high-voltage wire assembly includes an electrode connector at one end for releasably connecting to the AED electrode on the patient's body, and a plug at the other end for connecting to the AED.

ECG and AED connectors provide numerous benefits to patients and medical practitioners alike. One benefit is the ability to disconnect the patient from either the ECG monitor or the AED device without removing the electrode from the patient's body. This feature saves both costs associated with application of additional electrically conductive gel and/or adhesive, as well as saves the patient from additional discomfort associated with removal of the electrode.

In practice, medical practitioners are often required to attach or reattach ECG and AED connectors to the affixed ECG and AED electrodes, respectively. The pressure applied to engage the connector to the electrode can cause pain to the patient. Many industry standard snap contacts have an insertion force of three pounds, which may result in patient discomfort. In particular, patients who have significant injuries may be at risk to additional pain due to the pressure required to attach and/or reattach the connector to the electrode.

Medical practitioners who attempt to avoid causing additional pain to the patient may apply insufficient force to secure the connector to the electrode, thus creating loose connections and inaccurate results. Furthermore, substantial force may be required to disengage the connector from the electrode. The force required to decouple the connector may cause pain to the patient or result in the sudden removal of the electrode from the patient's skin, further inducing pain. Thus, improvements to connectors and electrodes are continually sought.

SUMMARY OF THE INVENTION

According to one aspect of the invention, an electrode lead wire connector that is configured to be connected to an electrode is provided. The electrode lead wire connector includes a one-piece electrically conductive connector contact having one end that is configured to be connected to a lead wire and an opposite end having an electrode receiving section that is configured to releasably receive a post of an electrode. The electrode receiving section includes a detent for retaining the post of the electrode within the electrode receiving section. Resilient engagement between the detent and the post provides a user of the electrode lead wire connector with tactile feedback indicating that the post of the electrode is fully engaged with the electrode receiving section of the one-piece electrically conductive connector contact.

According to another aspect of the invention, a kit comprises (a) at least one high-voltage electrode including a conductive post having a first diameter; (b) at least one low-voltage electrode including a conductive post having a second diameter that is larger than the first diameter; and (c) at least one high-voltage electrode lead wire connector that includes a first opening having a third diameter for receiving the conductive post of the at least one high-voltage electrode. The third diameter is less than the second diameter and greater than the first diameter to prevent the at least one high-voltage electrode lead wire connector from being connected to the conductive post of the at least one low-voltage electrode.

According to yet another aspect of the invention, an electrode lead wire connector is provided. The electrode lead wire connector includes a one-piece electrically conductive connector contact having one end that is configured to be connected to a lead wire and an opposite end having an electrode receiving section that is configured to releasably receive a post of an electrode. The one-piece electrically conductive connector is at least partially positioned in a covering. The covering defines (i) an outer surface that is positioned to face the electrode, (ii) an opening that is formed in the outer surface through which the post of the electrode is positioned to connect to the electrode receiving section of the one-piece electrically conductive connector contact, and (iii) a recess that is formed in the outer surface at a location that surrounds the opening. A non-conductive member is positioned in the recess, wherein the non-conductive member includes a hole that is sized to prevent a different sized post of another electrode from connecting to the electrode receiving section of the one-piece electrically conductive connector contact. One side of a double-sided adhesive is mounted to both the non-conductive member and the outer surface of the covering in order to retain the member in the recess. The other side of the double-sided adhesive is mountable to the electrode.

DETAILED DESCRIPTION OF THE INVENTION

Embodiments of the present invention will be become apparent herein and are intended to be only illustrative of the general principles of the invention. Various omissions, substitutions, and changes in the form and details of the device or process illustrated may be made by those skilled in the art without departing from either the scope or spirit of the invention. It is contemplated that the apparatuses that are disclosed herein will have apparent uses in other medical and non-medical devices.

Figure 1:
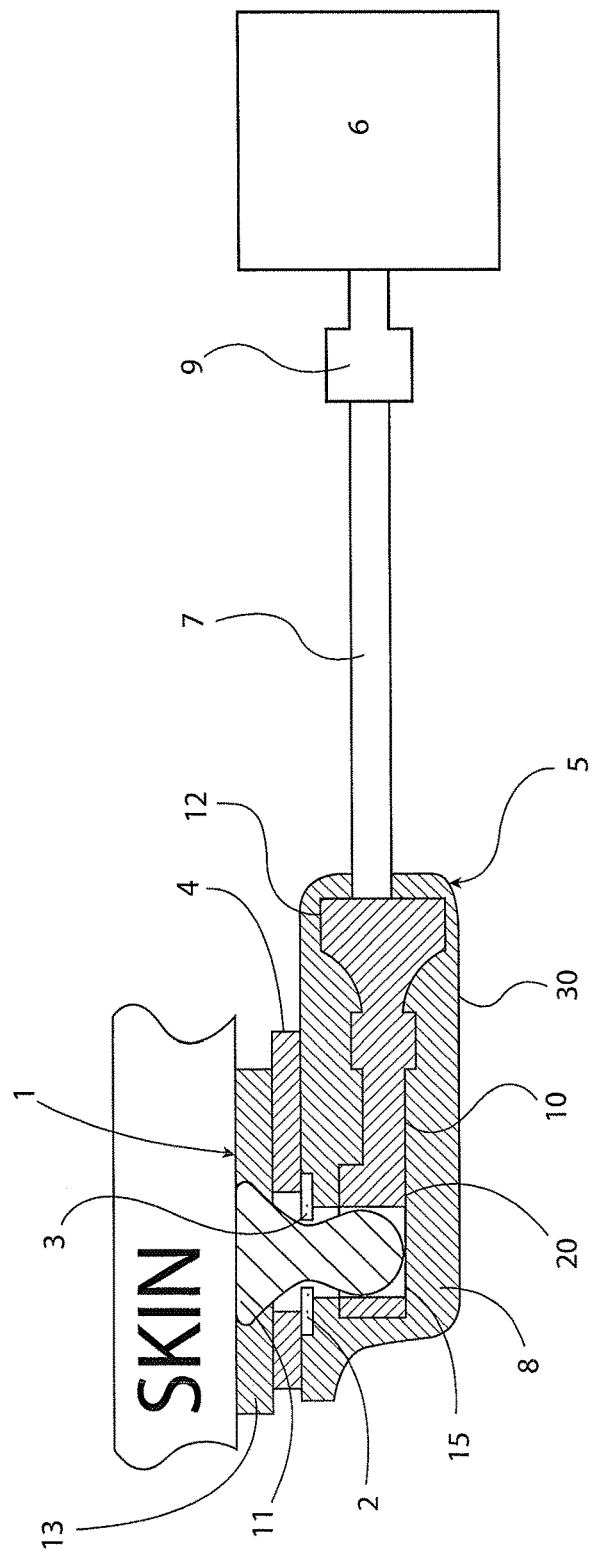
FIG. 1 is a schematic view of a high-voltage wire assembly that is interconnected between a high-voltage electrode, which is mounted to the skin of a patient's body, and a monitoring/defibrillation device. The high-voltage electrode and the high-voltage electrode lead wire connector are shown in cross-section.

FIG. 1 is a schematic view of a high-voltage wire assembly 5 that is interconnected between a high-voltage electrode 1, which is mounted to the skin of a patient (labeled 'SKIN'), and a defibrillation/monitoring device 6. The high-voltage electrode 1 and the high-voltage electrode lead wire connector 30 are shown in cross-section in FIG. 1. It should be understood that the high-voltage electrode 1 and the defibrillation/monitoring device 6 do not form part of the high-voltage wire assembly 5. The defibrillation/monitoring device 6 may be a defibrillation device, an AED device, an ECG monitor, or a Holter device, for example.

In operation, one or more high-voltage electrodes 1 are placed on the patient's skin, and each electrode 1 is attached to a lead wire connector 30 of a discrete wire assembly 5. Electricity is then transmitted by the device 6 through the wire assembly 5 (by way of the connector 9), through the conductive posts 11 of the electrode 1, and then to the patient's skin and heart.

Referring now to the features of the high-voltage electrode 1, the electrode 1 comprises a conductive post 11 that is at least partially embedded in an adhesive backed pad 13. The adhesive side of the adhesive backed pad 13 is positioned against the skin. The opposite side of the adhesive backed pad 13 may or may not include adhesive. The high-voltage electrode 1 may be a conventional, off-the-shelf AED or defibrillator electrode.

Referring now to the features of the high-voltage wire assembly 5, the wire assembly 5 generally includes a lead wire 7, a high-voltage lead wire connector 30 connected to one end of the lead wire 7, and a connector 9 mounted to an opposite end of the lead wire 7 for connection to the defibrillation/monitoring device 6. The connector 9 may be an industry-standard connector that is configured to be connected to the device 6. The connector 9 is an optional feature of the wire assembly 5.

The high-voltage lead wire connector 30 generally includes a one-piece connector contact 10 that is at least partially contained within a covering 8. The connector contact 10 includes an electrode receiving section 20 that is configured to be releasably connected to the conductive post 11 of the electrode 1. The connector contact 10 also includes a wire receiving section 12 that is connected to one end of a lead wire 7 by a crimp, weld and/or solder, for example. The wire 7 may be tinsel wire, stranded wire, or other common type of wire. Further details of the connector contact 10 are described with reference to FIGS. 3-7.

Figure 12A:
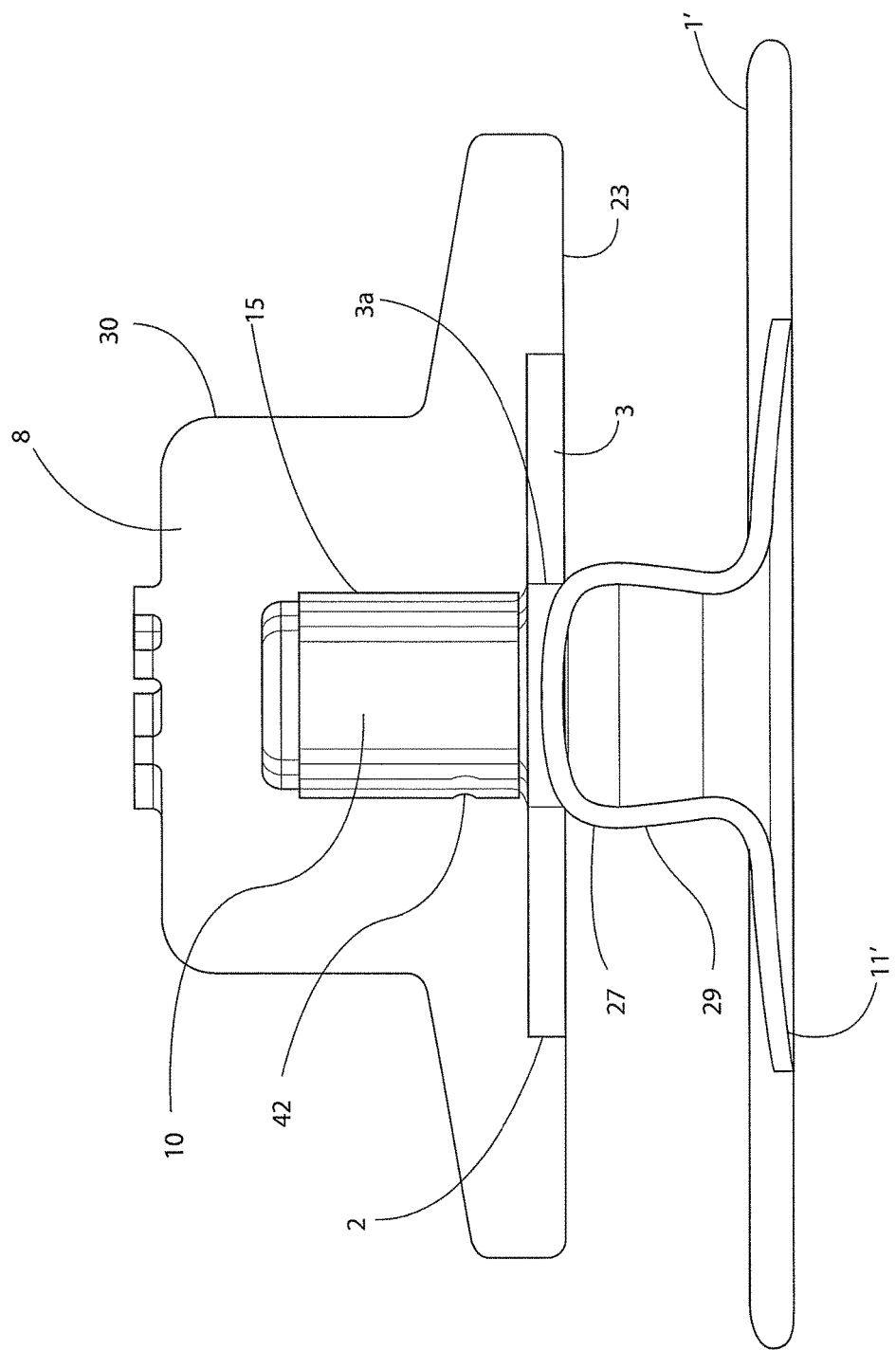
FIG. 12A shows a low-voltage ECG electrode not capable of being mounted to a high-voltage electrode lead wire connector.

As best shown in FIGS. 1 and 12A, the covering 8 includes a hole 15 on its exterior face 23 through which the conductive post 11 of the electrode 1 is configured to be inserted. A counterbore recess 2, which intersects the hole 15, is formed on the exterior face 23 at a location adjacent to the electrode 1. The counterbore recess 2 is sized to receive a rigid, non-conductive member 3 having a hole or opening 3a. The non-conductive member 3 may sit flush in the recess 2, as shown in FIG. 1, or it may protrude slightly from the recess 2 of the covering 8. Further details of the covering 8 are described with reference to FIGS. 8-11.

A double-sided adhesive 4 is mounted to the non-conductive member 3 and the outer surface of the covering 8. The adhesive 4 serves three functions, namely, (i) it retains the member 3 in the recess 2; (ii) it creates a water tight seal between the lead wire connector 30 and the electrode 1 such that liquid cannot penetrate the connector contact 10; and (iii) it adheres to the panel 13 of the electrode 1 thereby increasing the force required to remove the lead wire connector 30 from the electrode 1. Increasing the force required to remove the lead wire connector 30 from the electrode 1 inhibits inadvertent removal of the lead wire connector 30 from the electrode 1.

The bonding strength of the adhesive on the side of the double-sided adhesive 4 that faces the covering 8 may be greater than the bonding strength of the adhesive on the side of the double-sided adhesive 4 that faces the electrode 1. Using a stronger adhesive on the side that faces the covering 8 prevents the member 3 from becoming detached from the lead wire connector 30 upon removing the lead wire connector 30 from the electrode 1. Thus, the lead wire connector 30 and the wire assembly 5 may be reused, if so desired.

Although not shown, the member 3 may be permanently mounted in the recess 2 by another means, such as epoxy, to prevent it from becoming detached from the covering 8. As another alternative to the double-sided adhesive 4, and although not shown, a thin seal member could be molded into the exterior face 23 of the covering 8 to create a seal between the electrode pad 1 and the conductive post 11. Alternatively, the member 3 and its corresponding recess 2 could be omitted if the covering 8 were sufficiently rigid and non-conductive.

FIGS. 3-7 depict detailed views of the connector contact 10 of the high-voltage wire assembly 5. The connector contact 10 is formed from one continuous piece of conductive material, such as phosphor bronze, beryllium copper, aluminum, or spring steel, for example, which is bent into the configuration shown in FIGS. 3-7. The connector contact 10 is composed of electrically conductive material. The appendages of the connector contact 10 are bent into the positions shown in FIGS. 3-7.

The connector contact 10 generally includes the electrode receiving section 20 at one end thereof that is configured to be releasably connected to the conductive post 11 of the electrode 1. The opposite end of the connector contact 10 includes the wire receiving section 12 that is configured to be affixed to the wire 7. An arm 19 joins the wire receiving section 12 to the electrode receiving section 20.

The wire receiving section 12 includes two flange sets 14 and 16 that are configured to be crimped to the wire 7. Flange set 14, comprising flange 14a and 14b, originates from opposite sides of the wire receiving section 12. Flange set 16, comprising flange 16a and 16b (not shown in FIG. 3), also originates from opposite sides of the wire receiving section 12. The flanges 16 are positioned closer to the electrode receiving section 20 than are the flanges 14. A channel 18 extending between the flanges 14a and 14b, as well as flanges 16a and 16b, is provided for accommodating the wire 7.

According to one exemplary method of assembling the wire assembly 5, the sheath at one end of the wire 7 is stripped back by a pre-determined distance. The stripped end of the wire is positioned in the channel 18 such that stripped end of the wire 7 is positioned between the flanges 16, while the sheath of the wire 7 is positioned between the flanges 14. Thereafter, the flanges 14 are crimped to the sheath of the wire 7 and the flanges 16 are crimped to the stripped end of the wire 7. The wire 7 may also be soldered, welded or adhered to the flanges 14 and 16, if so desired.

The electrode receiving section 20 of the connector contact 10 includes a fixed end that is connected to the arm 19 and a 3-shaped free end. The 3-shaped free end is sized to releasably engage the post 11 of the electrode 1. The 3-shaped free end includes three curved segments 22a, 22b and 24. The post 11 is sized to be retained between the curved segments 22a and 22b. The curvature of the curved segments 22a and 22b matches the curvature of the bulbous portion 27 of the post 11, as is shown in FIG. 12A.

The curved segment 24 extends between the curved segments 22a and 22b. The curved shape of the curved segment 24 adds resiliency to the electrode receiving section 20 such that the curved portions 22a and 22b return to their initial position shown in FIG. 5 after the post 11 is removed from between the curved segments 22a and 22b.

Figure 5:
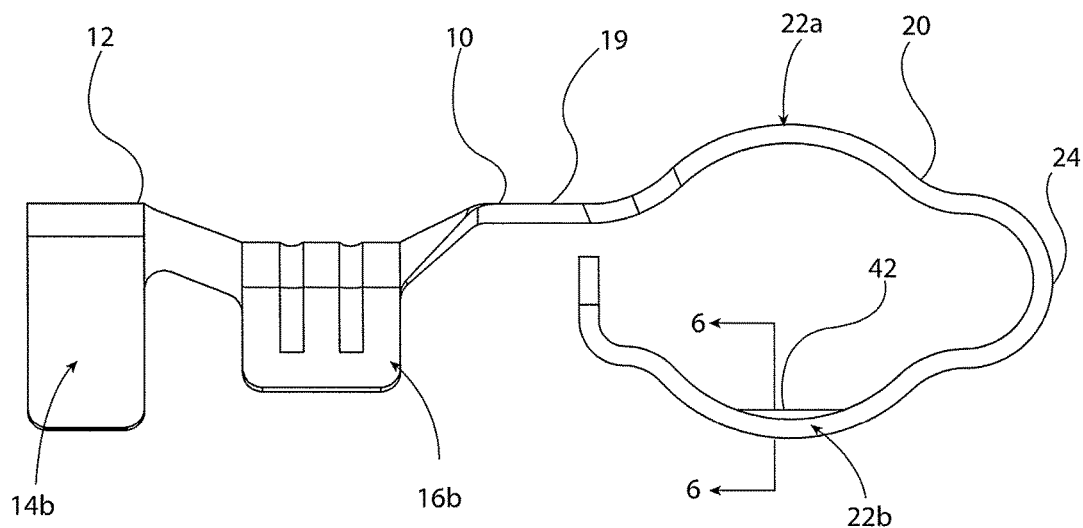
FIG. 5 is right side elevation view of the connector contact of FIG. 3.
Figure 6:
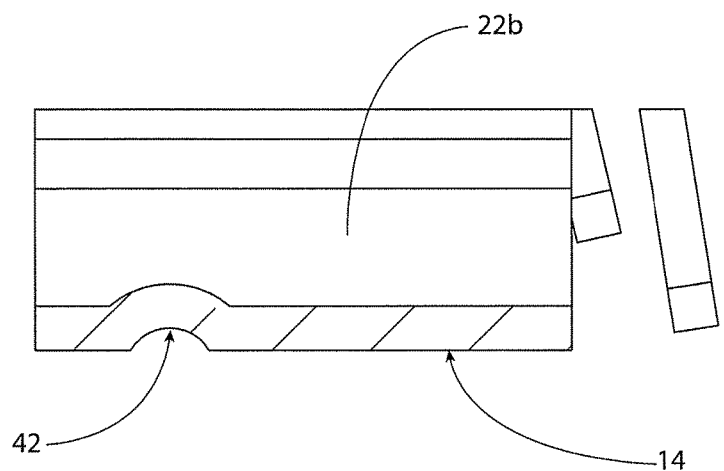
FIG. 6 is a cross-sectional view of the connector contact taken along the lines 6-6 in FIG. 5.
Figure 7:
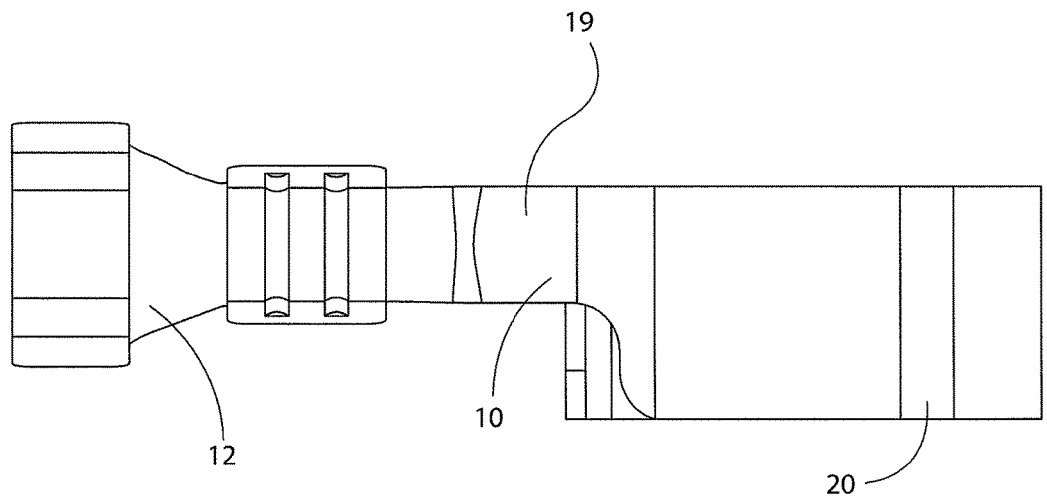
FIG. 7 is a top plan view of the connector contact of FIG. 3.
Figures 8, 9:
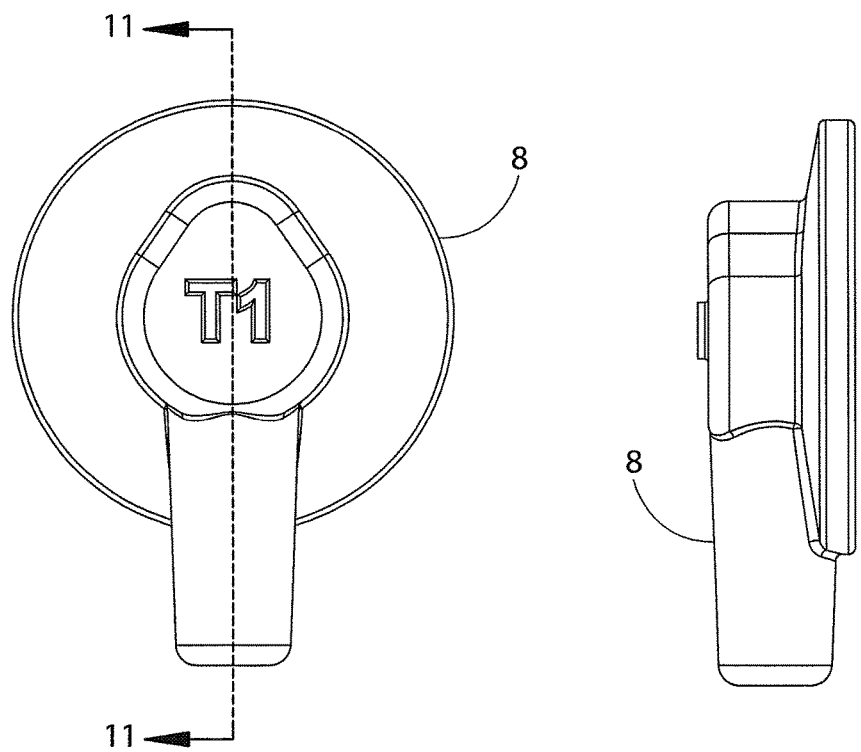
FIG. 8 is a rear elevation view of the covering of the high-voltage electrode lead wire connector of FIG. 1.
FIG. 9 is a side elevation view of the covering of FIG. 8.
Figure 10:
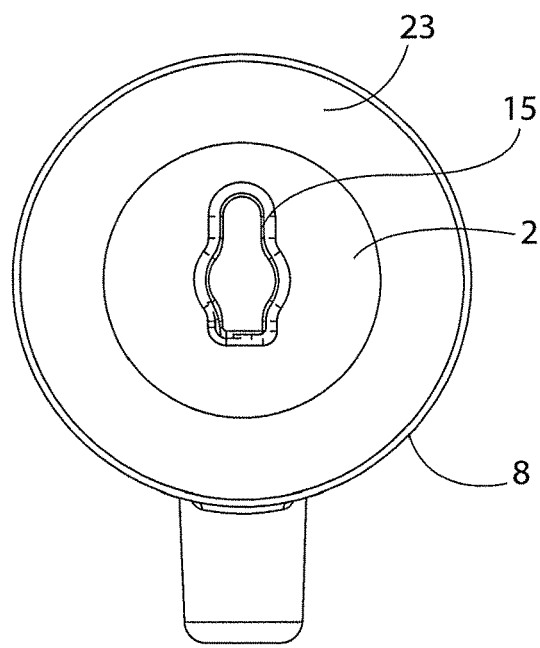
FIG. 10 is a front elevation view of the covering of FIG. 8.
Figure 11:
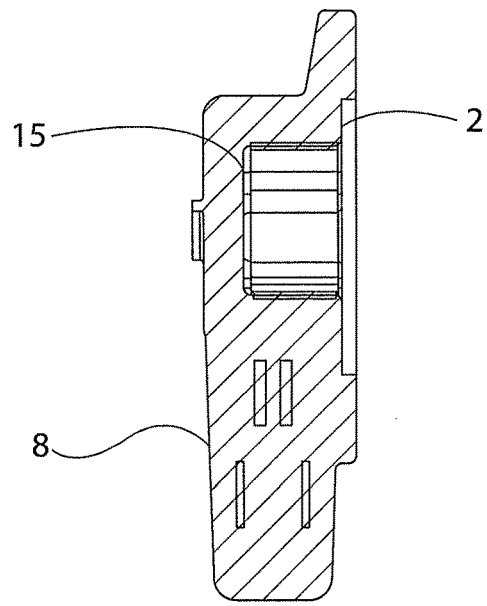
FIG. 11 is a cross-sectional view of the covering of FIG. 8 taking along the lines 11-11.
Figure 12B:
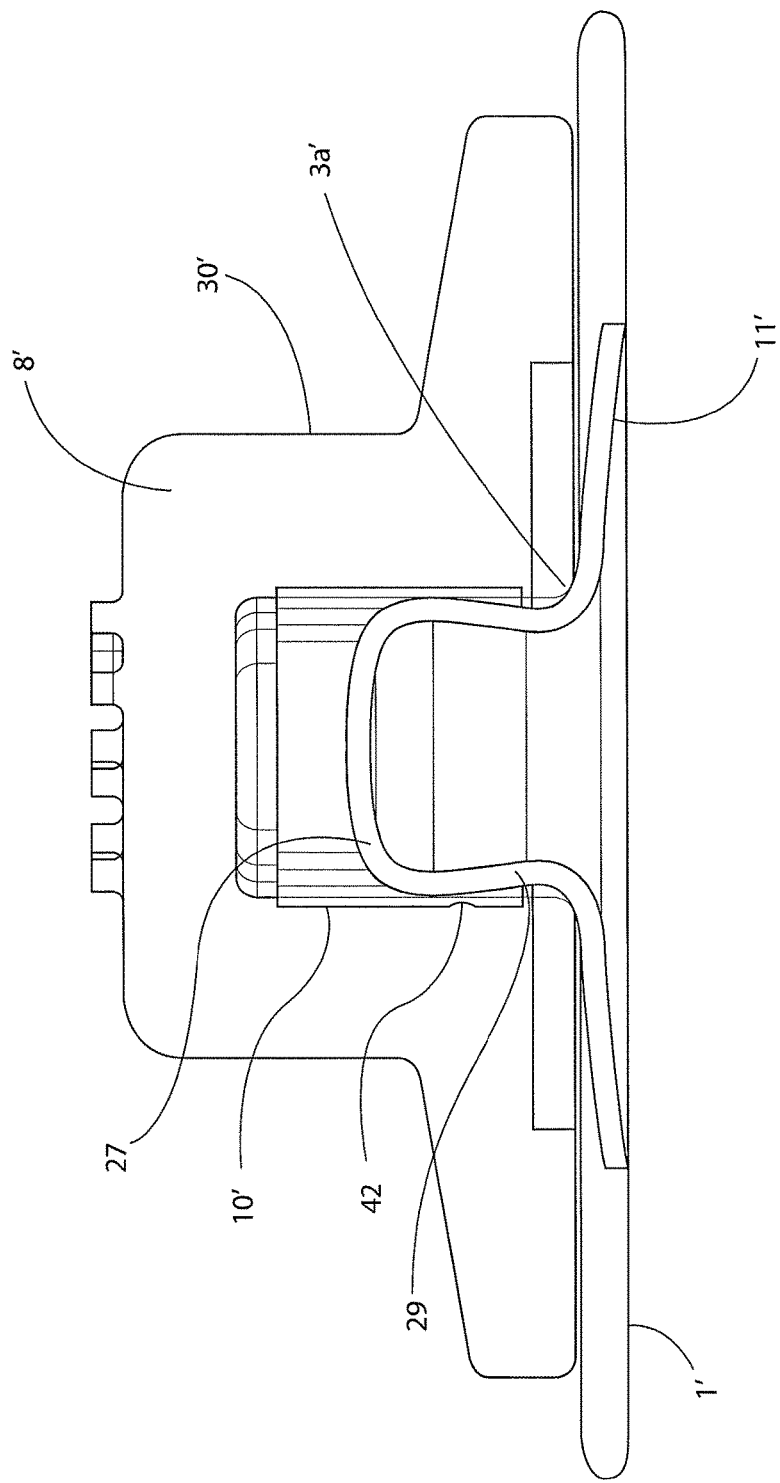
FIG. 12B shows a low-voltage ECG electrode mounted to a low-voltage ECG electrode lead wire connector.

FIGS. 5, 6 and 12B depict a detent 42 that is formed as an indentation on the outer surface 14 of the curved segment 22b. The detent 42 extends inwardly toward the spaced defined between the curved portions 22a and 22b. Alternatively, the detent 42 could be located on the curved portion 22a. As shown in FIG. 12B, the detent 42 is located on the curved portion 22a of the free end of the connector contact 10 such that the bulbous portion 27 of the post 11 rides over the detent 42 as the post 11 is inserted into the connector contact 10.

More particularly, as the bulbous portion 27 of the post 11 is inserted between the curved portions 22a and 22b of the connector contact 10, the bulbous portion 27 contacts the detent 42, which causes the curved portions 22a and 22b of the resilient connector contact 10 to expand and move apart. The curved portions 22a and 22b move apart until the lower concave side 29 of the bulbous portion 27 reaches the detent 42 at which point the curved portions 22a and 22b snap back and move closer together due to the resilient nature of the connector contact 10. A user can feel the bulbous portion 27 snap over the detent 42 during insertion of the electrode 1 into the lead wire connector 30. Thus, the detent 42 in conjunction with the resiliency of the connector contact 10 provide the user with a tactile signal indicating full engagement between the connector contact 10 and the electrode 1. Following insertion of the post 11, the lower concave side 29 of the bulbous portion 27 rests against the detent 42. The detent 42 retains the post 11 within the connector contact 10.

By virtue of the design of the one-piece connector contact 10, the lead wire connector 30 has an insertion force, i.e., the manual force that is required to connect the lead wire connector 30 to the electrode 1, of two pounds, whereas industry standard connectors have an insertion force of three pounds. The reduced insertion force results in less patient discomfort during the attachment of the lead wire connector 30 to the electrode 1 that is positioned on the patient's skin. The removal force of the lead wire connector 30 (i.e., the force required to disconnect the lead wire connector 30 from the electrode 1) is greater than the insertion force for the wire assembly 5.

FIGS. 8-11 depict detailed views of the covering 8 of the high-voltage wire assembly 5. The covering 8 includes a hole 15 through which the conductive post 11 of the electrode 1 is positioned. The boundaries of the hole 15 corresponds to the shape of the electrode receiving section 20 of the connector contact 10.

A recess 2, which intersects the hole 15, is formed on the outer surface 23 of the covering 8 that is positioned to face the electrode 1. The recess 2 is sized to receive the rigid, non-conductive member 3. The depth of the recess 2 may be sized such that the member 3 sits flush in the recess 2, as shown, or the recess 2 may be sized such that the member 3 protrudes slightly from the recess 2.

The covering 8 may be molded directly over the one-piece connector contact 10. The covering 8 may be composed of a plastic or rubber material, for example, having a low durometer. The covering 8 may be formed from a rigid, non-conductive material if so desired.

Figure 2A:
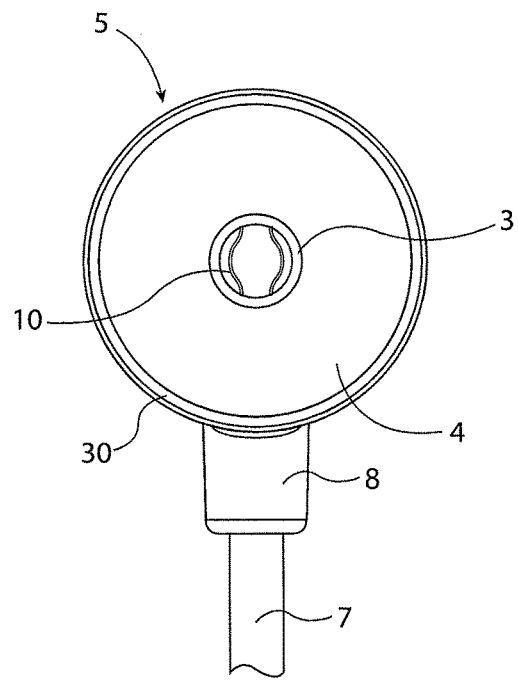
FIG. 2A is a bottom plan view of a segment of the high-voltage wire assembly of FIG. 1.
Figure 2B:
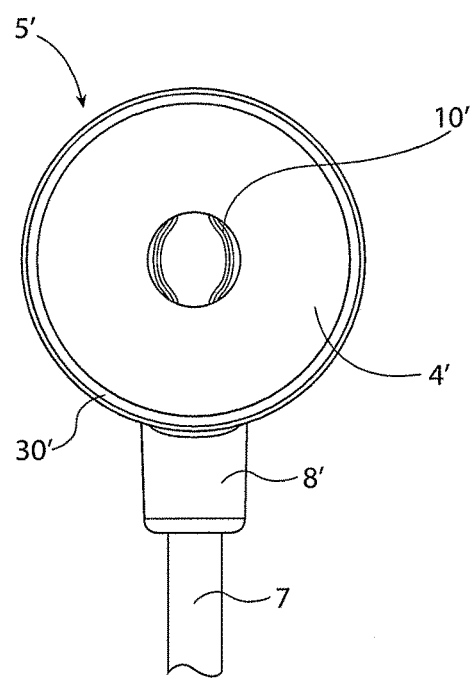
FIG. 2B is a bottom plan view of a segment of a low-voltage ECG wire assembly.
Figure 3:
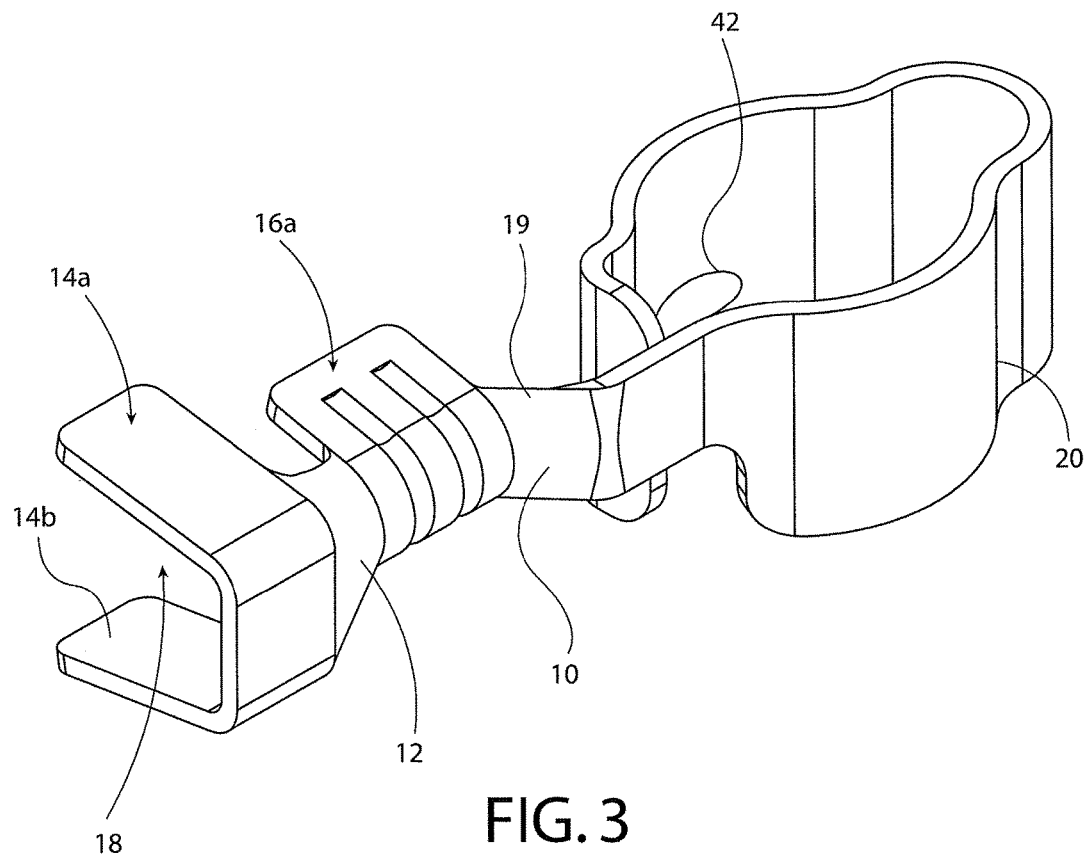
FIG. 3 is a perspective view of a high-voltage connector contact of the high-voltage electrode lead wire connector of FIG. 1 as viewed from the top and front sides of the connector contact.
Figure 4:
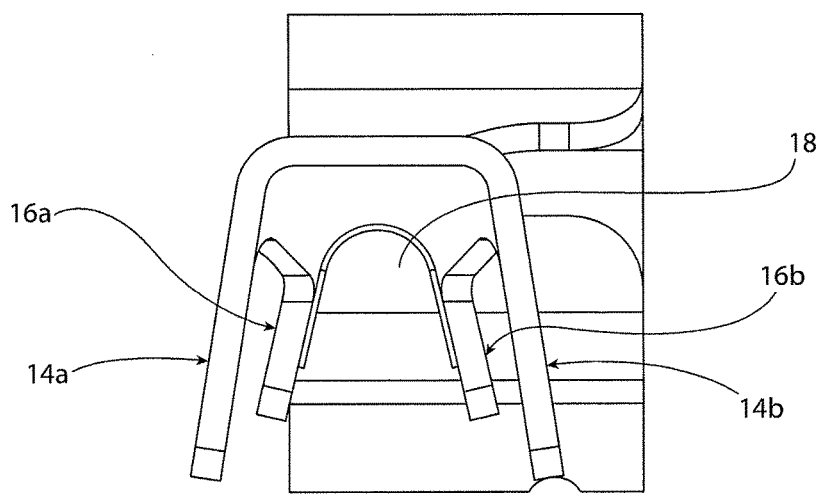
FIG. 4 is a front elevation view of the connector contact of FIG. 3.

FIGS. 2B and 12B depict a low-voltage ECG wire assembly 5'. The low-voltage ECG wire assembly 5' is similar to the high-voltage wire assembly 5 and only the differences between the assemblies 5 and 5' will be described hereinafter. Similar features of the low-voltage ECG wire assembly 5' are designated in FIGS. 2B and 12B by prime item numbers and those features may not be described herein for the purpose of conciseness.

The low-voltage ECG wire assembly 5' does not include a non-conductive member 3 and the connector contact 10' and covering 8' of the low-voltage ECG wire assembly 5' also differ from that of the high-voltage wire assembly 5. For example, as shown in FIG. 12B, the covering 8' of the low-voltage ECG wire assembly 5' does not include a recess 2 because the low-voltage ECG wire assembly 5' does not include the non-conductive member 3.

The low-voltage ECG wire assembly 5' is configured to be mated to a low-voltage ECG electrode 1' that is attached to the patient's body. In operation, electricity from the patient's body is conducted through the conductive post 11' of the ECG electrode 1', then conducted through the wire assembly 5' that is connected to each ECG electrode 1', and is ultimately conducted to the monitoring/defibrillation device 6 by the connector (like connector 9) of the wire assembly 5' that is coupled to the ECG monitoring/defibrillation device 6.

The high-voltage wire assembly 5 would ordinarily be used, for example, with high-voltage defibrillation devices, whereas the low-voltage wire assembly 5' would ordinarily be used with low voltage ECG monitoring devices. Moreover, the wire assemblies 5 and 5' could be used with an AED device that serves as both a defibrillation device and a monitoring device.

The lead wire connectors 30 and 30' of the wire assemblies 5 and 5' are structurally different in an effort to prevent the inadvertent connection of a high-voltage lead wire connector 30 to an ECG electrode 1' that is intended for a low-voltage application. In other words, the lead wire connectors 30 and 30' are structurally dissimilar to prevent the inadvertent connection of a high-voltage wire assembly 5, which may be intended for a high-voltage defibrillation, to an ECG electrode 1' that is intended for a low-voltage monitoring application.

Although not shown, the low-voltage wire assembly 5' and the high-voltage wire assembly 5 may be combined together as part of a single wire assembly that has both low-voltage monitoring and high-voltage defibrillation capabilities.

FIG. 12A shows how the non-conductive member 3 prevents a low-voltage conductive post 11' of a low-voltage ECG electrode 1' from contacting the connector contact 10 of the high-voltage wire assembly 5. Specifically, the small diameter opening 3a of the non-conductive member 3 of the high-voltage wire assembly 5 prevents the larger diameter conductive post 11' of a low voltage ECG electrode 1' from contacting the connector contact 10 of the high-voltage wire assembly 5. For the purpose of comparison, FIG. 12B shows how a low-voltage conductive post 11' is mated to the low-voltage connector contact 10' of the low-voltage ECG wire assembly 5'.

If the covering 8 were formed from a rigid, non-conductive material, then the non-conductive member 3 could conceivably be omitted from the high-voltage electrode lead wire connector 30, and the diameter of the hole 15 would be resized to match the diameter of the opening 3a of the non-conductive member 3 in order to prevent the high-voltage electrode lead wire connector 30 from contacting a low-voltage ECG electrode 1'.

The above-described wire assemblies 5 and 5' may be provided in kit form as an electrode and connector kit. Referring to FIGS. 12A and 12B, an electrode and connector kit would comprise the following components:

- at least one high-voltage electrode 1 intended for defibrillation including a conductive post 11 having a first diameter;
- at least one low-voltage ECG electrode 1' intended for monitoring including a conductive post 11' having a second diameter that is larger than the first diameter;
- at least one high-voltage electrode lead wire connector 30 that includes a first opening 3a having a third diameter for receiving the conductive post 11 of the at least one high-voltage electrode 1, wherein the third diameter is less than the second diameter and greater than the first diameter to prevent the at least one high-voltage electrode lead wire connector 30 from being connected to the conductive post 11' of the at least one low-voltage ECG electrode 1'; and
- at least one low-voltage ECG electrode lead wire connector 30' that includes a second opening 3a' (see FIG. 12B) having a fourth diameter for receiving the conductive post of the at least one low-voltage ECG electrode, wherein the fourth diameter is greater than the second diameter.

The electrode lead wire connector 30 and 30' may be provided in the kit either with or without the wires 7 and connectors 9 that are shown in FIG. 1.

It will be understood that various modifications may be made to the embodiments disclosed herein. Further variations, including the addition, substitution, or omission of features, functions, or alternatives thereof, are contemplated herein. Moreover, incorporation into other different systems, instruments, applications, or methods of production thereof are also contemplated.

What is claimed:

1. An electrode lead wire connector that is configured to be connected to an electrode for defibrillation and/or heart monitoring comprising:
   a one-piece electrically conductive connector contact having one end that is configured to be connected to a lead wire and an opposite end having an electrode receiving section that is configured to expand upon releasably connecting to a conductive post of the electrode,
   wherein the electrode receiving section of the connector contact includes a detent for retaining the post of the electrode within the electrode receiving section, and resilient engagement between the detent and the post provides a user of the electrode lead wire connector with tactile feedback indicating that the post of the electrode is fully engaged with the electrode receiving section of the one-piece electrically conductive connector contact,
   wherein the electrode receiving section is curved and has an inwardly facing surface that is configured to contact the post, and the detent is an indentation on the inwardly facing surface that protrudes inwardly toward the post.

2. The electrode lead wire connector of claim 1 further comprising a covering in which the one-piece electrically conductive connector is at least partially positioned.

3. The electrode lead wire connector of claim 2, wherein the covering defines an outer surface that is positioned to face the electrode, and an opening that is formed in the outer surface through which the post of the electrode is positioned to connect to the electrode receiving section of the one-piece electrically conductive connector contact.

4. The electrode lead wire connector of claim 3, wherein a recess is formed in the outer surface of the covering at a location that surrounds the opening.

5. The electrode lead wire connector of claim 4 further comprising a non-conductive member that is positioned in the recess, wherein the member includes an opening that is sized to prevent a larger sized post of another electrode from connecting to the electrode receiving section of the one-piece electrically conductive connector contact.

6. The electrode lead wire connector of claim 5 further comprising a double-sided adhesive pad having first and second adhesive sides, the first adhesive side being mounted to both the non-conductive member and the outer surface of the covering in order to retain the member in the recess, and the second adhesive side being mountable to the electrode.

7. The electrode lead wire connector of claim 6, wherein an adhesive strength of the first adhesive side is greater than an adhesive strength of the second adhesive side of the double-sided adhesive pad to either limit or prevent the double-sided adhesive pad from becoming detached from the member and the outer surface of the covering upon removing the electrode lead wire connector from the electrode.

8. The electrode lead wire connector of claim 3 further comprising a double-sided adhesive pad, one side of which is mounted to the outer surface of the covering, and the other side of which is mountable to the electrode.

9. An electrode lead wire connector that is configured to be connected to an electrode for defibrillation and/or heart monitoring comprising:
   a one-piece electrically conductive connector contact having one end that is configured to be connected to a lead wire and an opposite end having an electrode receiving section that is configured to expand upon being releasably connected to a conductive post of an electrode;
   a covering in which the one-piece electrically conductive connector is at least partially positioned, wherein the covering defines (i) an outer surface that is positioned to face the electrode, (ii) an opening that is formed in the outer surface through which the post of the electrode is positioned to connect to the electrode receiving section of the one-piece electrically conductive connector contact, and (iii) a recess that is formed in the outer surface at a location that surrounds the opening; and
   a non-conductive member that is positioned in the recess, wherein the non-conductive member includes an opening that is sized to prevent a larger sized post of another electrode from connecting to the electrode receiving section of the one-piece electrically conductive connector contact,
   wherein the electrode receiving section includes a detent for retaining the post of the electrode within the electrode receiving section and resilient engagement between the detent and the post provides a user of the electrode lead wire connector with tactile feedback indicating that the post of the electrode is fully engaged with the electrode receiving section of the one-piece electrically conductive connector contact, and
   wherein the electrode receiving section is curved and has an inwardly facing surface that is configured to contact the post, and the detent is an indentation on the inwardly facing surface that protrudes inwardly toward the post.

10. The electrode lead wire connector of claim 9 further comprising a double-sided adhesive pad, one side of which is mounted to both the non-conductive member and the outer surface of the covering in order to retain the non-conductive member in the recess, and the other side of which is mountable to the electrode.

* * * * *